United States Patent
Hae et al.

(10) Patent No.: US 11,849,533 B2
(45) Date of Patent: Dec. 19, 2023

(54) CIRCULAR ACCELERATOR, PARTICLE THERAPY SYSTEM WITH CIRCULAR ACCELERATOR, AND METHOD OF OPERATING CIRCULAR ACCELERATOR

(71) Applicant: Hitachi, Ltd., Tokyo (JP)

(72) Inventors: Takamitsu Hae, Tokyo (JP); Takayoshi Seki, Tokyo (JP); Kazuyoshi Saitou, Tokyo (JP); Fumiaki Noda, Tokyo (JP); Takamichi Aoki, Tokyo (JP); Kazuo Hiramoto, Tokyo (JP)

(73) Assignee: HITACHI, LTD., Tokyo (JP)

(*) Notice: Subject to any disclaimer, the term of this patent is extended or adjusted under 35 U.S.C. 154(b) by 0 days.

(21) Appl. No.: 18/062,056

(22) Filed: Dec. 6, 2022

(65) Prior Publication Data

US 2023/0105721 A1 Apr. 6, 2023

Related U.S. Application Data

(62) Division of application No. 16/761,307, filed as application No. PCT/JP2018/041159 on Nov. 6, 2018, now Pat. No. 11,570,881.

(30) Foreign Application Priority Data

Jan. 29, 2018 (JP) ................................. 2018-012145

(51) Int. Cl.
*H05H 7/10* (2006.01)
*H05H 7/04* (2006.01)
(Continued)

(52) U.S. Cl.
CPC ................ *H05H 7/10* (2013.01); *H05H 7/04* (2013.01); *H05H 13/02* (2013.01); *H05H 2007/087* (2013.01); *H05H 2277/11* (2013.01)

(58) Field of Classification Search
None
See application file for complete search history.

(56) References Cited

U.S. PATENT DOCUMENTS

| 2,576,108 | A | * | 11/1951 | Engelmann | H01J 25/56 |
| | | | | | 315/39.75 |
| 2,812,463 | A | | 11/1957 | Teng et al. | |

(Continued)

FOREIGN PATENT DOCUMENTS

| CN | 102651942 A | 8/2012 |
| JP | H01-239800 A | 9/1989 |

(Continued)

OTHER PUBLICATIONS

International Search Report, dated Jan. 22, 2019, which issued during the prosecution of International Application No. PCT/JP2018/041159, which corresponds to the present application.

(Continued)

*Primary Examiner* — Srinivas Sathiraju
(74) *Attorney, Agent, or Firm* — Baker Botts L.L.P.

(57) ABSTRACT

In a circular accelerator that applies a radiofrequency wave in a main magnetic field to accelerate charged particle beam while increasing an orbit radius, another radiofrequency wave with a frequency different from the radiofrequency wave used for acceleration is applied to the charged particle beam in order to extract the charged particle beam. Thereby, in the circular accelerator that accelerates charged particle beam while increasing an orbit radius by applying a radiofrequency wave in a main magnetic field, the high precision control on extraction of the charged particle beam from the circular accelerator is achieved.

16 Claims, 13 Drawing Sheets

(51) Int. Cl.
*H05H 13/02* (2006.01)
*H05H 7/08* (2006.01)

(56) References Cited

U.S. PATENT DOCUMENTS

| | | | | |
|---|---|---|---|---|
| 5,576,602 A * | 11/1996 | Hiramoto | ............ | A61N 5/1077 315/501 |
| 5,783,914 A * | 7/1998 | Hiramoto | ................ | H05H 7/10 315/504 |
| 5,969,367 A * | 10/1999 | Hiramoto | ............ | A61N 5/1042 315/501 |
| 6,462,348 B1 * | 10/2002 | Gelbart | ................... | G21K 1/14 250/505.1 |
| 7,394,082 B2 * | 7/2008 | Fujimaki | ................ | G21K 5/04 250/397 |
| 7,439,528 B2 * | 10/2008 | Nishiuchi | ................ | H05H 7/06 250/492.1 |
| 7,692,168 B2 * | 4/2010 | Moriyama | ............ | A61N 5/1048 250/492.3 |
| 8,368,038 B2 * | 2/2013 | Balakin | ................... | H05H 7/04 378/68 |
| 8,525,448 B2 * | 9/2013 | Tanaka | ................... | H05H 13/02 315/501 |
| 8,525,449 B2 * | 9/2013 | Torikai | ................... | H05H 13/04 315/504 |
| 8,581,525 B2 * | 11/2013 | Antaya | ................ | H05H 13/005 315/501 |
| 9,055,662 B2 * | 6/2015 | Kleeven | ................ | H05H 13/005 |
| 9,095,040 B2 * | 7/2015 | Balakin | ................... | H05H 7/10 |
| 9,185,790 B2 * | 11/2015 | Svedberg | ............ | H05H 13/005 |
| 9,271,385 B2 * | 2/2016 | Verbruggen | ............ | H05H 13/02 |
| 9,456,487 B2 * | 9/2016 | Takase | ................... | H05H 7/02 |
| 9,550,077 B2 * | 1/2017 | Tsoupas | ................... | H05H 7/10 |
| 9,579,525 B2 * | 2/2017 | Balakin | ................ | A61N 5/1067 |
| 9,615,441 B2 * | 4/2017 | Bromberg | ................ | H05H 7/02 |
| 9,622,335 B2 * | 4/2017 | Gall | ................ | A61N 5/1077 |
| 9,649,510 B2 * | 5/2017 | Balakin | ................ | A61N 5/1067 |
| 9,848,487 B2 * | 12/2017 | Kleeven | ................... | G06F 30/00 |
| 9,867,272 B2 * | 1/2018 | Lal | ................... | H01J 37/06 |
| 9,894,747 B2 * | 2/2018 | Pärnaste | ................ | H05H 13/005 |
| 10,306,745 B2 * | 5/2019 | Aoki | ................... | A61N 5/10 |
| 10,368,429 B2 * | 7/2019 | Gall | ................... | A61N 5/1077 |
| 10,548,212 B2 * | 1/2020 | Aoki | ................ | H05H 13/04 |
| 10,624,201 B2 * | 4/2020 | Aoki | ................... | H05H 15/00 |
| 10,946,219 B2 * | 3/2021 | Tahar | ................ | A61N 5/1077 |
| 2007/0252093 A1 * | 11/2007 | Fujimaki | ................ | G21K 5/04 250/492.3 |
| 2012/0200237 A1 * | 8/2012 | Torikai | ................ | H05H 7/10 315/503 |
| 2013/0105702 A1 * | 5/2013 | Balakin | ................ | H05H 13/04 250/396 ML |
| 2013/0249443 A1 * | 9/2013 | Antaya | ................ | H05H 13/005 315/502 |
| 2014/0028220 A1 * | 1/2014 | Bromberg | ............ | H05H 13/005 315/502 |
| 2014/0094643 A1 | 4/2014 | Gall et al. | | |
| 2016/0270204 A1 * | 9/2016 | Bromberg | ................ | H05H 7/10 |
| 2017/0303384 A1 * | 10/2017 | Aoki | ................... | H05H 13/04 |
| 2017/0318657 A1 * | 11/2017 | Aoki | ................... | H05H 13/005 |
| 2017/0339778 A1 * | 11/2017 | Aoki | ................... | H05H 7/10 |
| 2019/0070438 A1 * | 3/2019 | Tahar | ................... | H05H 13/085 |
| 2019/0239333 A1 * | 8/2019 | Aoki | ................... | H01F 7/202 |
| 2019/0269941 A1 * | 9/2019 | Aono | ................... | A61N 5/1065 |
| 2021/0195725 A1 * | 6/2021 | Hae | ................... | H05H 13/005 |
| 2021/0196984 A1 * | 7/2021 | Hae | ................... | H05H 7/04 |

FOREIGN PATENT DOCUMENTS

| | | |
|---|---|---|
| JP | 10-118204 A | 5/1998 |
| JP | 2002-305100 A | 10/2002 |
| JP | 2017-192796 A | 10/2017 |
| JP | 2017-220460 A | 12/2017 |

OTHER PUBLICATIONS

W. Kleeven et al., "The IBA Superconducting Synchrocyclotron Project S2C2," Proceeding of Cyclotrons 2013, pp. 115-119.
K. J. Le Couteur, "The Regenerative Deflector for Synchro-Cyclotrons," Proceedings of the Physical Society, Section B, 64, 1951, pp. 1073-1084.
S. Kurashima, et al., "Progress in Formation of Single-Pulse Beams by a Chopping System at the JAEA/TIARA Facility," Proceedings of Cyclotrons 2010, pp. 233-235.
Notice of Reasons for Refusal, dated Mar. 30, 2021, for Japanese Patent Application No. 2018-012145 (with English translation).

* cited by examiner

CIRCULAR ACCELERATOR, PARTICLE THERAPY SYSTEM WITH CIRCULAR ACCELERATOR, AND METHOD OF OPERATING CIRCULAR ACCELERATOR

TECHNICAL FIELD

The present invention relates to a particle circular accelerator, a particle beam therapy using the same, and a method of operating the circular accelerator.

BACKGROUND ART

A circular accelerator which circularly moves and accelerate beams is often used in particle therapy. In particular, a synchrocyclotron using superconducting coils is effective at reducing the size and costs for therapy facilities. Nonpatent Literature 1 discloses a synchrocyclotron used in particle therapy. A beam in the synchrocyclotron circulates in a temporally constant main magnetic field while increasing the curvature radius of orbit, so that the beam has energy and is accelerated every time the beam passes through an acceleration gap in which an acceleration radiofrequency electric filed is produced at some midpoint of orbit. Since the main magnetic field is a non-isochronous magnetic field, the acceleration radiofrequency electric field is required to be frequency modulated in order to maintain the acceleration conditions, and a certain frequency modulation pattern is repeated in an acceleration cycle of the order of msec. Thus, an acceleration cycle is repeated, in which when the injected beam is accelerated to the maximum energy, the beam is extracted from the accelerator.

Patent Literature 1 discloses a scanning irradiation method commonly used in particle therapy. A patient target volume is irradiated with the extracted beam through an irradiation system. At this time, if in the scanning irradiation method commonly used in particle therapy, a scanning coil is used to scan the beam in a direction perpendicular to the beam travel direction in conformity to the target shape. Also, in the beam travel direction, the beam energy is changed to adjust a range in order to perform irradiation in conformity to the target shape.

CITATION LIST

Patent Literature

Patent Literature 1: Japanese Unexamined Patent Application Publication No. Hei 10(1998)-118204 Nonpatent Literature
Nonpatent Literature 1: W. Kleeven, "The IBA Superconducting Synchrocyclorton Project S2C2", Proceeding of Cyclotrons 2013

SUMMARY OF INVENTION

Technical Problem

In the synchrocyclotron of Nonpatent Literature 1, an acceleration cycle is repeated, in which the beam injected into the accelerator is accelerated to reach the maximum energy, and then the beam is extracted to the outside of the accelerator by a regenerator. Specifically, an acceleration cycle is repeated, in which the beam with a pulsed time structure is injected in a single pulse and the pulsed beam is extracted from the 1 pulse accelerator. The amount of beam to be extracted relies on the amount of pulses to be injected and the process of acceleration and extraction. Therefore, it is difficult to control arbitrarily the length of beam pulse to be extracted and the amount of charge. Also, the amount of beam charge to be extracted is dependent on temporal variation in the amount of ion generated at the ion source, temporal stability of the acceleration radiofrequency electric field, and the like. Therefore, there is an issue of variations of the amount of beam charge to be extracted from acceleration cycle to acceleration cycle.

Here, in the scanning irradiation, for the purpose of preventing a target volume from undergoing insufficient/excessive irradiation, the high precision dose control is required for each irradiation spot. However, in the case of the scanning irradiation in the synchrocyclotron, as described above, it is difficult to use only single pulse beam charge extracted within a single acceleration cycle to apply a required dose of irradiation for a spot without excess and deficiency. A possible method is contemplated, in which the extracted beam charge is reduced by intention by adjusting the ion source to reduce the injected beam charge, by reducing the acceleration radiofrequency voltage, and/or the like, and thus the low charge beam is extracted in pulses for irradiation of a dose for a spot. However, in the method, a dose rate which is the amount of irradiation per unit time is decreased. This increases the time required for treatment at a single time, and in turn patient throughput suffers.

To address the above, it is an object to achieve high precision control on extraction of charged particle beam from a circular accelerator, in the circular accelerator that applies a radiofrequency wave in a main magnetic field in order to accelerate the charged particle beam while increasing an orbit radius.

Solution to Problem

In a circular accelerator that applies a radiofrequency wave in a main magnetic field in order to accelerate charged particle beam while increasing an orbit radius, another radiofrequency wave with a frequency different from the radiofrequency wave used for acceleration is applied to the charged particle beam in order to extract the charged particle beam.

Advantageous Effects of Invention

By applying the present invention to a circular accelerator that applies a radiofrequency wave in a main magnetic field in order to accelerate charged particle beam while increasing an orbit radius, the radiofrequency wave used for extraction is able to be used to control the extracted beam charge in each acceleration cycle with high precision.

DESCRIPTION OF EMBODIMENT

Embodiments according to the present invention will now be described with reference to the accompanying drawings. It should be understood that the following description is provided as exemplary embodiments for illustrative purpose, and the subject matter of the invention is not intended to be limited to any specific aspect described below. The invention itself may be modified to provide various forms in addition to exemplary embodiments described below.

Also, a circular accelerator according to the present invention is capable of minutely controlling the amount of beam to be extracted. Therefore, the circular accelerator according to the present invention is suitable for used in a particle therapy system, in particular, a particle therapy system using scanning irradiation techniques, but is not limited to application to such particle therapy systems.

First Embodiment

A description will be given of a circular accelerator according to a first embodiment which is one of preferred embodiments according to the present invention. The circular accelerator 39 according to the embodiment accelerates proton beam by a frequency modulated radiofrequency electric field in a main magnetic field of temporally constant intensity. The extracted beam has energy of 235 MeV, for example.

Figure 1:
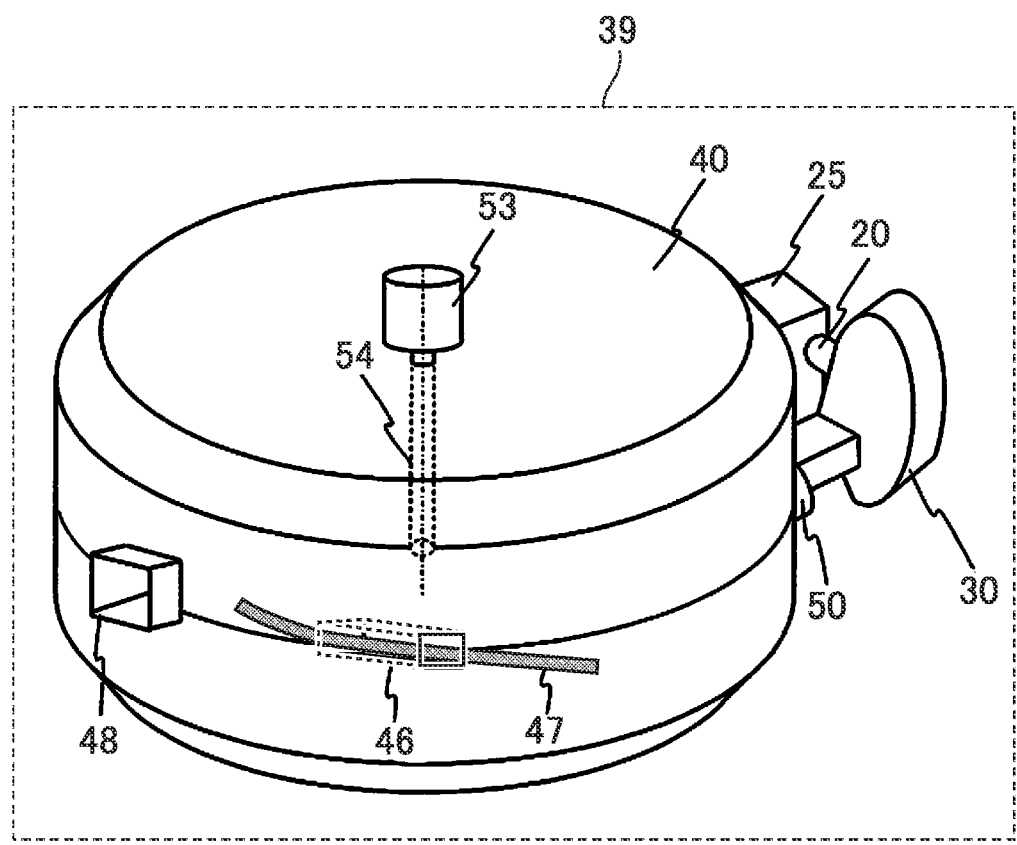
FIG. 1 is an external view of a circular accelerator according to a first embodiment.
Figure 2:
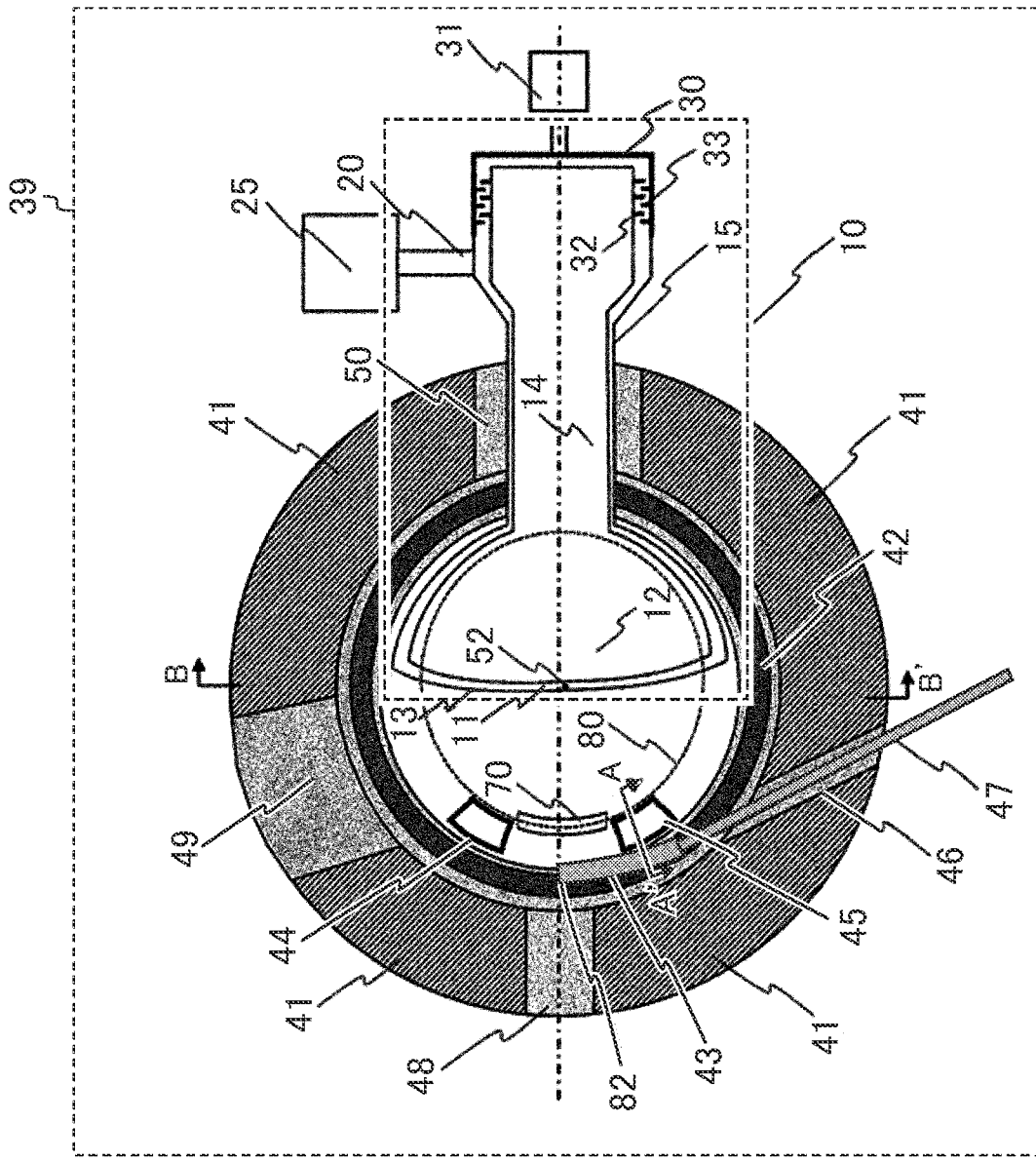
FIG. 2 is a cross sectional structure of the circular accelerator according to the first embodiment.
Figure 3:
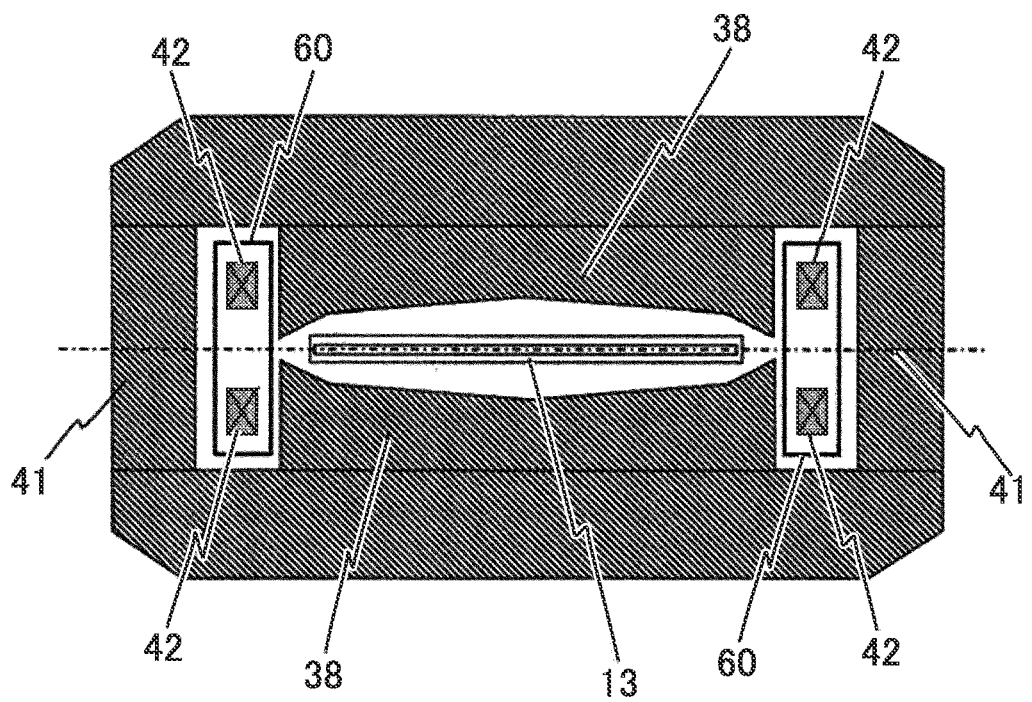
FIG. 3 is a sectional view taken on arrows B-B' of FIG. 2.

FIG. 1 illustrates the outer appearance of the circular accelerator 39. FIG. 2 illustrates a configuration diagram of a cross section of the circular accelerator 39. FIG. 3 illustrates a configuration diagram of a vertical section (a sectional view taken on arrows B-B' of FIG. 2) of the circular accelerator 39.

The circular accelerator 39 has an outer shell formed by a vertical separable main electromagnet 40, and a vacuum is drawn on a beam acceleration region within the main electromagnet 40.

An ion source 53 is installed on an upper portion of the main electromagnet 40, and the ion source 53 generates ion beam to be injected into the main electromagnet 40. The beam generated at the ion source 53 passes through a low energy beam transport 54 and then is injected into the beam acceleration region in the main electromagnet 40 by an ion injector 52 placed around the center of an upper main magnetic pole 38. An ECR ion source or the like may be suitably used as the ion source 53. It is noted that the ion source 53 may be placed within the vacuum beam acceleration region in the main electromagnet 40, and in this case, use of a PIG ion source or like may be suitable.

The main electromagnet 40 includes main magnetic poles 38 (see FIG. 6), a yoke 41 and main coils 42. The yoke 41 forms the outer appearance of the main electromagnet 40 and includes an approximately cylindrical region formed therein. The main coils 42 are ring-shaped coils, which are placed along the inner wall of the yoke 41. The main coils 42 are superconducting coils, which are cooled by a cryostat 60 placed around the main coils 42. On the inner circumference side of the main coils 42, the main magnetic poles 38 are placed to face each other in the vertical direction. Upon the passage of electric current, the main coils 42 are excited, allowing the main magnetic poles 38 to form a magnetic field in the vertical direction, which is referred to as a main magnetic field. Also, the acceleration region means a region for accelerating the beam in the main magnetic field.

The yoke 41 has a plurality of through ports. Among the through ports, a beam through port 46 for extraction of the accelerated beam; a coil through port 48 through which various coil conductors are routed to exit from the inside of the yoke 41 to the outside; a vacuuming through port 49; and a radiofrequency through port 50 for a radiofrequency acceleration cavity 10 are located in a bonding face between the upper and lower magnetic poles.

The radiofrequency acceleration cavity 10 is a λ/2 resonance cavity, which has a dee electrode 12, a dummy dee electrode 13, an inner conductor 14, an outer conductor 15 and a rotating capacitor 30. The dee electrode 12 is a D-shaped hollow electrode, which is connected with the inner conductor 14. The dummy dee electrode 13 is an earth potential electrode, which is connected with the outer conductor 15 externally wrapping the inner conductor 14. The shape of the dummy dee electrode 13 is not required to be a D-shaped hollow shape and an acceleration gap 11 is formed between the dee electrode 12 and the dummy dee electrode 13.

An input coupler 20 is equipment for providing radiofrequency power to the radiofrequency acceleration cavity 10, which is connected to the inner conductor 14 by means of electrostatic coupling or magnetic coupling. Power is supplied to the input coupler 20 from an acceleration radiofrequency power supply 25, and radiofrequency power is provided to the inner conductor 14 through the input coupler 20 from outside. Thereby, a radiofrequency acceleration voltage for accelerating the beam is generated in the acceleration gap 11 between the dee electrode 12 and the dummy dee electrode 13, and thus a radiofrequency electric field is generated by the radiofrequency acceleration voltage.

The rotating capacitor 30 is equipment for modulating the resonance frequency of the radiofrequency acceleration cavity 10, which includes a motor 31, a stationary electrode 32, and a rotating electrode 33 facing the stationary electrode 32. The stationary electrode 32 is formed on the inner conductor 14. The rotating electrode 33 also is adjacent to the outer conductor 15, and the rotating electrode 33 is not physically connected to the outer conductor 15 but is electrically connected to the outer conductor 15 through electrostatic capacitance. It is noted that the stationary electrode 32 may be formed on the outer conductor 15, and the rotating electrode 33 may be configured to be electrostatically coupled to the inner conductor 14.

In the rotating capacitor 30, the rotating electrode 33 is rotated by the motor 31 to effect a change in facing area of the stationary electrode 32 and the rotating electrode 33, thereby causing temporal changes in electrostatic capacitance formed between the stationary electrode 32 and the rotating electrode 33. Such temporal changes in electrostatic capacitance cause a change in resonance frequency of the radiofrequency acceleration cavity 10 to form a frequency modulation pattern. An acceleration voltage frequency modulated by the rotating capacitor 30 occurs in the acceleration gap 11 between the dee electrode 12 and the dummy dee electrode 13. FIG. 2 illustrates the acceleration gap 11 in the case where the number of harmonics is one, i.e., the circulation frequency and the acceleration frequency are equal, the acceleration gap 11 being formed in accordance with beam orbit geometry.

The circular accelerator 39 has, as equipment for beam extraction, a radiofrequency kicker 70, a septum coil 43 and a high energy beam transport 47. The accelerated beam is extracted from the beam extraction path entrance 82 to outside the acceleration region. The septum coil 43 is disposed in the beam extraction path entrance 82. It is noted that the septum coil 43 may be divided into two or more divisions arranged in the beam travel direction. The high energy beam transport 47 for transporting the extraction beam from within the main electromagnet 40 to an outside is disposed next to the septum coil 43 to extend through the beam through port 46 to the outside of the main electromagnet 40. The radiofrequency kicker 70 is equipment to apply a radiofrequency voltage to the circulating beam passing through the inside of the radiofrequency kicker 70. The septum coil 43 is a coil for bending the beam toward the outer circumference in the horizontal direction, which has a coil conductor 43-1 and a coil conductor 43-2. The septum coil 43 borders the acceleration region across the coil conductor 43-1. By passing electric current through the coil conductors 43-1, 43-2, a magnetic field in a direction perpendicular to the closed orbit of the beam occurs within the septum coil 43. By the magnetic field, the beam traveling into the septum coil 43 is bent to travel toward the high energy beam transport 47. It is noted that the septum coil 43 may include a magnetic material core such as an iron core. Also, as an alternative to the septum coil 43, as long as the incoming beam can be bent toward high energy beam transport 47, a passive configuration using only a magnetic material and/or a permanent magnet without any coil may be employed.

Within the main electromagnet 40, also, a peeler magnetic field region 44 and a regenerator magnetic field region 45 are formed, which are a disturbance magnetic field including a dipole magnetic field and a multipole magnetic field. Used for the beam extraction are the radiofrequency kicker 70, the peeler magnetic field region 44, the regenerator magnetic field region 45, the septum coil 43 and the high energy beam transport 47. The beam extraction will be described in detail later.

Here, a brief description is given of a movement of the beam from injection to extraction of the beam in the circular accelerator 39.

First, charged particle beam generated at the ion source 53 passes through the low energy beam transport 54 and then is injected into the beam acceleration region within the main electromagnet 40 by the ion injector 52. The injected beam is accelerated in the radiofrequency electric field, and circulates in the main magnetic field while increasing in energy. As the beam is accelerated, the curvature radius of orbit of the beam is increased, so that the beam travels in a spiral orbit from the center of the acceleration region toward the outside.

Here, in the beam acceleration region, orbits in which the beam begins being accelerated and reaches maximum energy (e.g., 235 MeV) are referred to as closed orbits. Of the closed orbits, an orbit through which the maximum energy beam passes is referred to as a maximum energy orbit 80. Also, a plane in which the closed orbits make a spiral is referred to as an orbit plane or an orbital plane. Also, in a two-dimensional polar coordinate system of the orbital plane with the center of the acceleration region as an origin, the axis in the radially outward direction from the center is defined as an r axis.

In this orbital travel, the charged particles of the beam oscillate in a direction perpendicular to the beam orbit, and the oscillations are referred to as betatron oscillations and an oscillation frequency of the oscillations is referred to as a betatron frequency. Also, the oscillation frequency per orbit is referred to as a tune, and displacement on the r axis of the beam toward the outside of the orbit plane per orbit is referred to as turn separation. Also, for the circulating beam, the betatron oscillations in the orbit plane and in a direction perpendicular to the beam orbit is referred to as horizontal betatron oscillations, and the tune is referred to as a horizontal tune. The betatron oscillations have the property of, upon application of an appropriate radiofrequency voltage, producing resonance to cause a steep increase in amplitude.

The main magnetic field may be an AVF (Azimuthal Varying Field) type as well as of a type to have a constant main magnetic field intensity in the circumferential direction. In either case, since the main magnetic field distribution is a non-isochronous magnetic field, the beam stabilization condition is satisfied, in which an n value expressed by equation (1) is greater than zero and less than 1.

$$n = -\frac{\rho}{|B|}\frac{\partial B}{\partial r} \qquad (1)$$

where $\rho$ is a bending radius of the design orbit, B is a magnetic field intensity, and $\partial B/\partial r$ is a magnetic field gradient in the radial direction. Under the beam stabilization conditions described above, the beam minutely offset from the design orbit in the radial direction undergoes a restoring force to return to the design orbit, and simultaneously the beam offset in a direction perpendicular to the orbit plane also undergoes a restoring force from the main magnetic field in the direction that returns to the orbit plane. That is, the beam produces the betatron oscillations in proximity to the design orbit, so that stable circulation and acceleration of the beam are enabled. Also, a value close to 1 is set for a betatron frequency (horizontal tune) $v_r$ parallel to the orbit plane and also in a direction perpendicular to the orbit, for the full energy beam.

The above-described main magnetic field distribution is formed by the main magnetic poles 38, and pole pieces (not shown) and/or trim coils (not shown) installed on the surface of the main magnetic poles 38. Since the constituent elements forming the main magnetic field distribution are disposed symmetrically with respect to the orbital plane, the main magnetic field has, on the orbital plane, only a magnetic field component in a direction perpendicular to the orbital plane.

When the beam is accelerated in the main magnetic field to the maximum energy, the radiofrequency acceleration voltage for accelerating the beam into the acceleration gap 11 is stopped, and the beam circulates on the maximum energy orbit 80. When the beam enters the radiofrequency kicker 70 installed on the maximum energy orbit 80 to apply a radiofrequency wave, a radiofrequency voltage is applied to increase the betatron oscillation amplitude of the beam.

The beam with increased betatron oscillation amplitude then reaches the peeler magnetic field region 44 and the regenerator magnetic field region 45 which are located some distance from the maximum energy orbit 80 on the outer circumference side of the maximum energy orbit 80. The beam reaching the peeler magnetic field region 44 is kicked toward the outer circumference of the orbit plane, and the beam reaching the regenerator magnetic field region 45 is kicked toward the inner circumference of the orbit plane. As used herein, the term "kick" means that a beam is bent by being applied with an electric field or a magnetic field. Through the kick by a quadrupole magnetic field component of the peeler magnetic field region 44, as the beam further increases in betatron oscillation amplitude, the turn separation is increased. At the same time, the magnetic field of the regenerator magnetic field region 45 prevents the horizontal tune of the beam from abruptly varying, and then until the beam is extracted, the betatron oscillations spread in a vertical direction at a 90-degree angle to the horizontal direction, to prevent a beam loss. Upon a sufficient turn separation being obtained, the beam enters the septum coil 43, then is kicked outward of the orbit plane to travel through the high energy beam transport 47, and then is extracted to the outside of the circular accelerator 39.

The range of increase in turn separation by the peeler magnetic field region 44 and the regenerator magnetic field region 45 is significantly greater than that by the radiofrequency kicker 70. Therefore, adjusting the radiofrequency voltage to be applied by the radiofrequency kicker 70 allows adjustment of the amount of beam reaching the peeler magnetic field region 44 and the regenerator magnetic field region 45, of the beam circulating on the maximum energy orbit 80. That is, in conventional circular accelerators, after the beam has reached the maximum energy, the full beam is extracted without control on the amount of extracted charge. In contrast, the radiofrequency application to the radiofrequency kicker 70 is stopped during the beam extraction, so that no beam reaches the peeler magnetic field region 44 and the regenerator magnetic field region 45. This enables an interruption of the beam extraction from the circular accelerator 39. Resuming the application to the radiofrequency kicker 70 enables resumption of beam extraction.

Also, the intensity of the beam to be extracted from the circular accelerator 39 can be controlled by controlling any one of intensity of voltage to be applied to the radiofrequency kicker 70, an amplitude, a phase and a frequency of the radiofrequency wave.

Further, in conventional circular accelerators, the amount of beam charge to be extracted varies from pulse to pulse due to temporal variations in the amount of ion generated at the ion source, temporal stability of the acceleration radiofrequency electric field, and/or the like. In contrast, in the present techniques, by adjusting the voltage to be applied to the radiofrequency kicker 70, factors exerting influences on the stabilities of the beams can be absorbed and the amount of charge in the extraction beam can be controlled with high precision.

Figure 4:
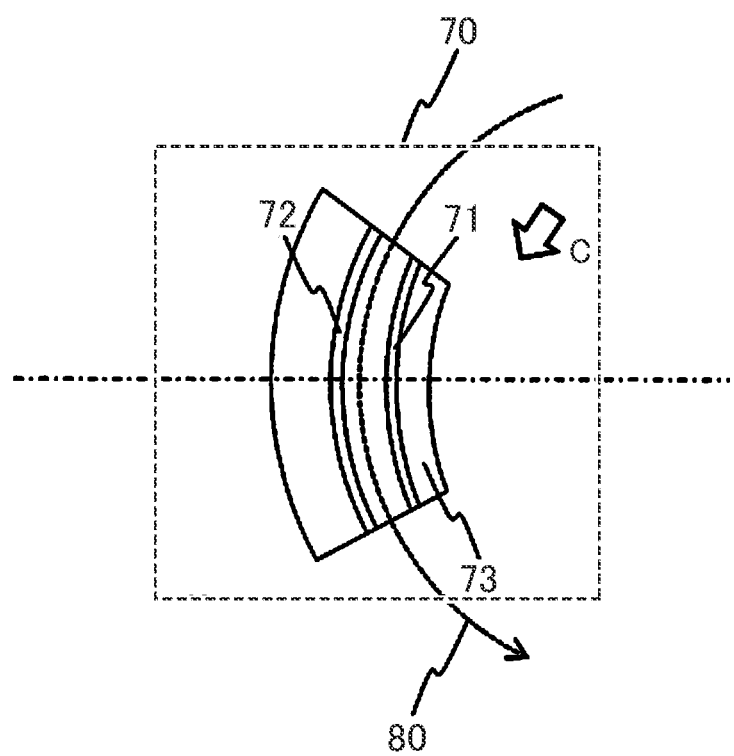
FIG. 4 is a cross sectional structure of a radiofrequency kicker according to the first embodiment.
Figure 5:
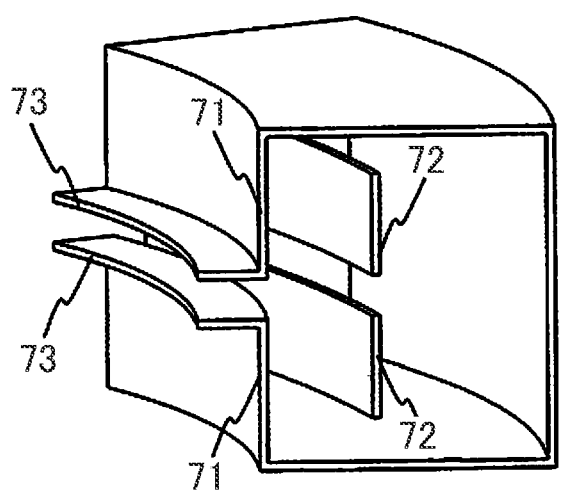
FIG. 5 is a bird's-eye view of the radiofrequency kicker as seen from B of FIG. 4.

FIG. 4 is a cross sectional structure of the radiofrequency kicker 70. Also, FIG. 5 is a bird's-eye view of the radiofrequency kicker 70 as seen from C of FIG. 4. The radiofrequency kicker 70 includes ground electrodes 71 and high voltage electrodes 72. Both the electrodes are located to face each other on opposite sides of the maximum energy orbit 80, with the ground electrodes 71 located on the inner circumference side and the high voltage electrodes 72 located on the outer circumference side. And, each of the ground electrodes 71 and the high voltage electrodes 72 has a shape that allows the radiofrequency electric field to act in a direction perpendicular to the orbit in the orbit plane, that is, the ground electrodes 71 and the high voltage electrodes 72 are each defined as a shape approximately parallel to the curve of the maximum energy orbit 80. Each ground electrode 71 also may have a metal made protrusion 73 attached thereto, in order to enhance the concentration of the radiofrequency electric field generated between the ground electrode 71 and the high voltage electrode 72. The high voltage electrode 72 applied with the radiofrequency voltage is insulated and supported. Within the cylindrically shaped acceleration region, the beam travels along the orbit plane around the middle in the height direction of the cylinder. The ground electrode 71 and the high voltage electrode 72 both have passage ports around the orbital plane through which the beam passes. Allowing for beam expansion by the betatron oscillations, each passage port may have a size enough to prevent beam collision. The radiofrequency kicker 70 according to the embodiment has a shape with an open end face as illustrated in FIG. 5, but may be formed in resonance structure by use of a ground electrode to block the end face except the beam passage port. The radiofrequency kicker 70 is located, for example, in the vicinity of the beam extraction path entrance 82 as illustrated in FIG. 2, but the radiofrequency kicker 70 may be located anywhere as long as it is on the maximum energy orbit 80.

The peeler magnetic field region 44 and the regenerator magnetic field region 45 are regions where a multipole magnetic field acting on the beam exists. The multipole magnetic field contains at least quadrupole magnetic field component, and may contain a multipole magnetic field with four or more poles, or alternatively a dipole magnetic field. The peeler magnetic field region 44 has a magnetic field gradient in a direction that weakens the main magnetic field toward the outer circumference in the radial direction, whereas the regenerator magnetic field region 45 has a magnetic field gradient in a direction that strengthen the main magnetic field toward the outer circumference in the radial direction. It is noted that, as the peeler magnetic field region 44, a region where the main magnetic field at a magnetic pole tip decreases may be utilized. The peeler magnetic field region 44 and the regenerator magnetic field region 45 are respectively located in azimuth angle regions on the outer circumference side of the maximum energy orbit 80, with the azimuth angle regions located on opposite sides of the beam extraction path entrance 82. Also, for the purpose of preventing the beam from traveling into the peeler magnetic field region 44 or the regenerator magnetic field region 45 before the betatron oscillation amplitude is increased by the radiofrequency kicker 70, the peeler magnetic field region 44 and the regenerator magnetic field region 45 are desirably located, on the outer circumference side, at a longer spacing from the maximum energy orbit 80 than that corresponding to the amplitude before the resonance of the betatron oscillations. Further, it is desirable that the peeler magnetic field region 44 is located upstream in the beam travel direction and the regenerator magnetic field region 45 is located downstream, and vice versa. It is noted that FIG. 2 illustrates a single peeler magnetic field region 44 and a single regenerator magnetic field region 45, but peeler magnetic field regions 44 and regenerator magnetic field regions 45 may be placed in multiple sites within the main magnetic field.

In the vicinity of the peeler magnetic field region 44 and the regenerator magnetic field region 45, multiple pole pieces, coils or both, which are formed of magnetic substances, are placed and secured with non-magnetic materials to form a desired multipole magnetic field. For example, for each of the peeler magnetic field region 44 and the regenerator magnetic field region 45, the multiple pole pieces are used to form a multipole magnetic field and the multiple coils are used to form a dipole magnetic field. The multiple pole pieces and coils may be located close to each other or may be located in spatially separated places.

Figure 6:
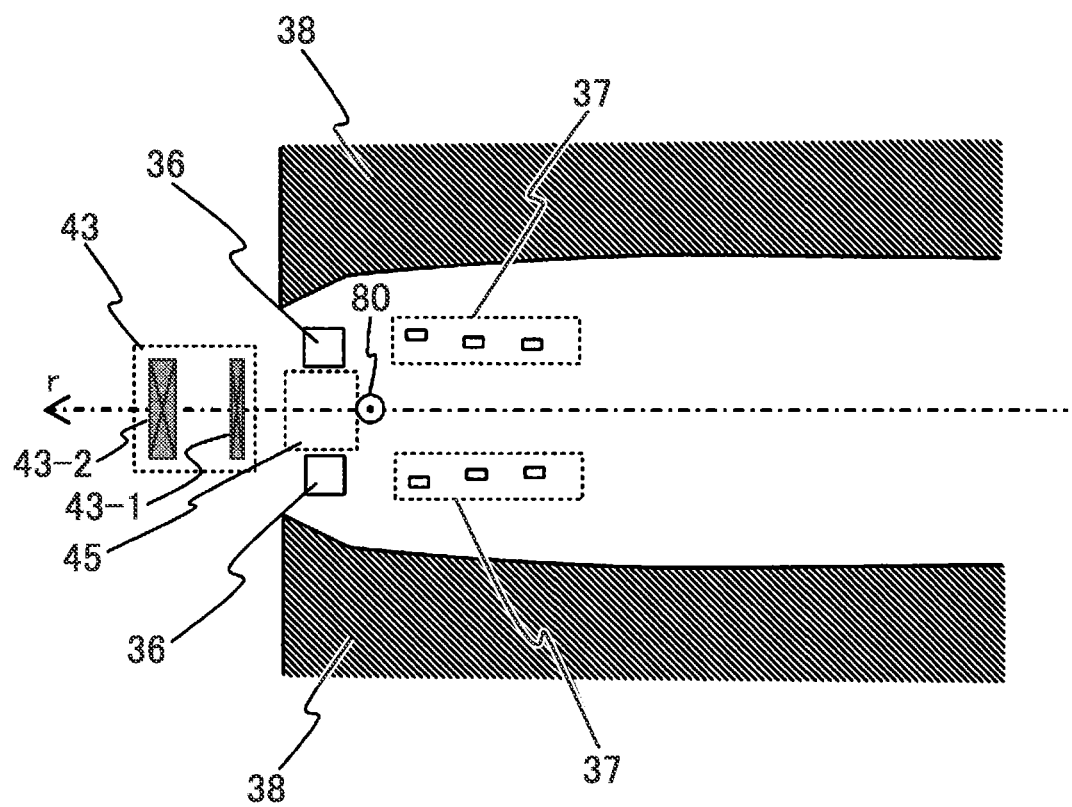
FIG. 6 is a sectional view taken on arrows A-A' of FIGS. 2 and 10.

FIG. 6 illustrates an example pole piece arrangement of the regenerator magnetic field region 45, which is a sectional view taken on arrows A-A' of FIG. 1. Used as pole pieces are: a magnetic field gradient shim 36 producing a magnetic field gradient in the regenerator magnetic field region 45; and a magnetic field correction shim 37 for canceling an unwanted magnetic field produced on the inner circumference side of the maximum energy orbit 80 by the magnetic field gradient shim 36. Also, FIG. 6 describes the regenerator magnetic field region 45 by way of example. Regarding the peeler magnetic field region 44, the peeler magnetic field region 44 also uses: a magnetic field gradient shim 36 producing a magnetic field gradient; and a magnetic field correction shim 37 for canceling an unwanted magnetic field produced on the inner circumference side of the maximum energy orbit 80 by the magnetic field gradient shim 36.

Figure 7:
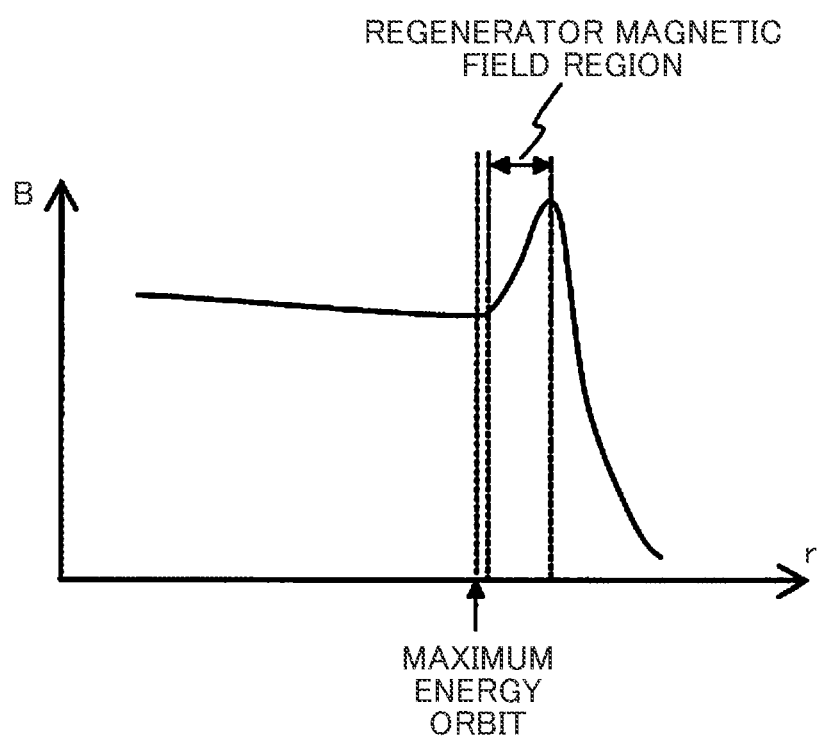
FIG. 7 is a distribution chart of a main magnetic field on straight line r of FIG. 6.

FIG. 7 illustrates a distribution of the main magnetic field on the r axis in FIG. 6. A magnetic field gradient $\partial B/\partial r$ declines slightly until the maximum energy orbit 80, and an n value in equation (1) satisfies the stabilization condition, so that the beam circulates with stability. However, in the regenerator magnetic field region 45, the magnetic field gradient rises sharply, so that the beam becomes unstable and is kicked toward the inner circumference of the orbit plane. Also, as opposed to the regenerator magnetic field region 45, in the peeler magnetic field region 44, the magnetic field gradient declines sharply, so that, in the peeler magnetic field region 44, the beam also becomes unstable and is kicked toward the outer circumference of the orbit plane.

It is noted that the range of increase in the betatron oscillation amplitude by the radiofrequency kicker 70 is smaller than the range of increase in the betatron oscillation amplitude by the peeler magnetic field region 44 and the regenerator magnetic field region 45. Even if the peeler magnetic field region 44 and the regenerator magnetic field region 45 are not provided, the effect of increasing the betatron oscillation amplitude by the radiofrequency kicker 70 enables the extraction of beam.

Figure 8:
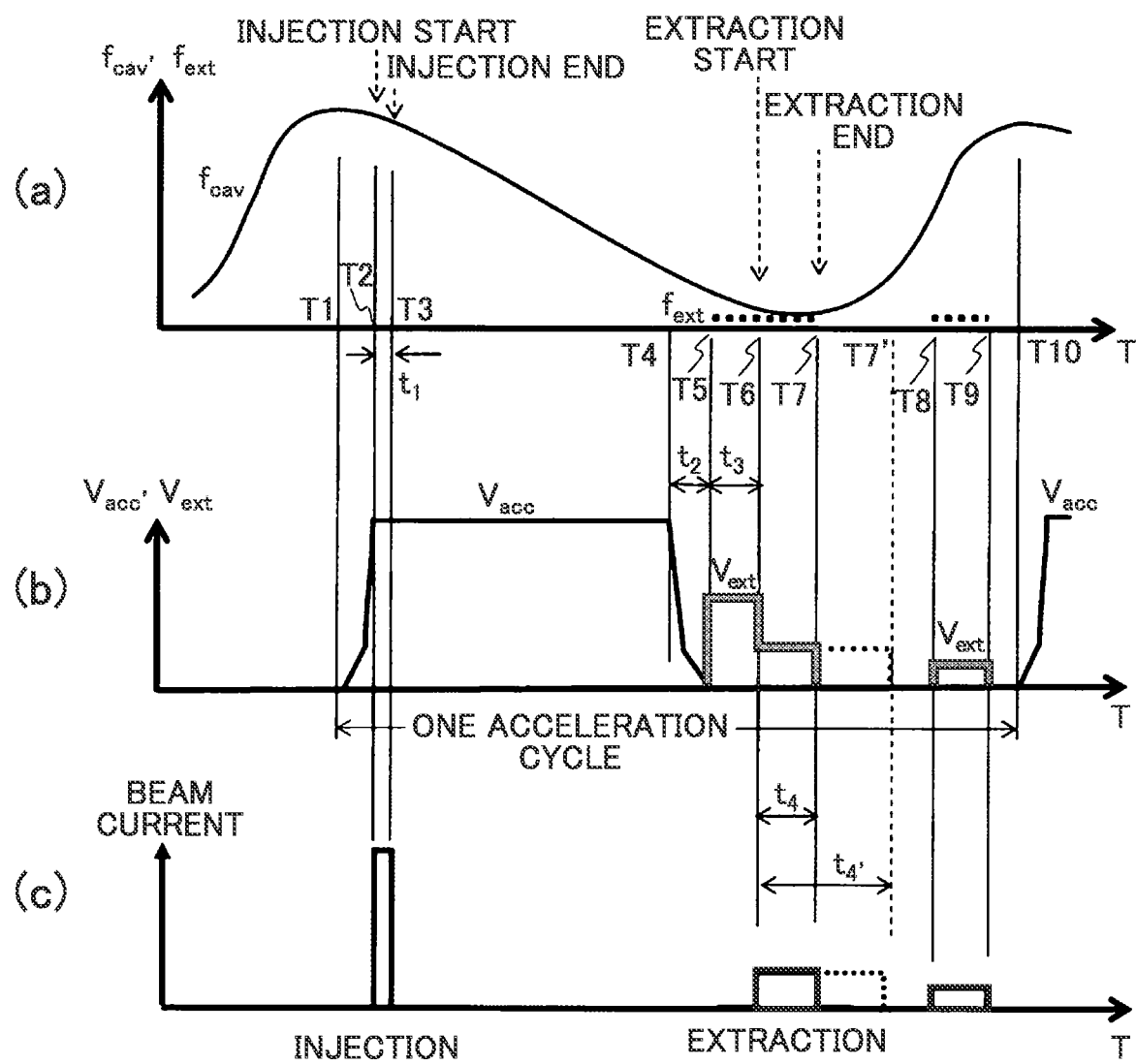
FIG. 8 is a diagram illustrating an accelerator operation pattern according to the first embodiment.

FIG. 8 is a diagram illustrating a procedure to extract the beam. FIG. 8(a) is a graph representing the relationship among a resonance frequency $f_{cav}$ of the radiofrequency acceleration cavity 10, a radiofrequency kicker frequency $f_{evt}$ which is a frequency of a radiofrequency electric field applied to the beam by the radiofrequency kicker 70, and time T. FIG. 8(b) is a graph representing the relationship among an acceleration voltage $V_{acc}$ generated in the acceleration gap 11, a radiofrequency kicker voltage $V_{ext}$ applied to the radiofrequency kicker 70, and time T. FIG. 8(c) is a graph representing the relationship among a current of the beam to be injected, a current of the beam to be extracted, and the time T.

An acceleration cycle begins with a rise of the acceleration voltage $V_{acc}$ (time T1). Then, upon the acceleration voltage $V_{acc}$ raising sufficiently, a beam is injected from the ion source 53 (time T2). After a lapse of time period t1 from the beam injection, a radiofrequency capture of the beam ends. The captured beam, that is, a beam, ready to be accelerated, of the injected beam, begins to be accelerated by the acceleration voltage $V_{acc}$ (time T3). Upon the beam reaching a maximum energy of 235 MeV, interruption of the acceleration radiofrequency wave is started (time T4), then after a lapse of time period $t_2$ therefrom, the acceleration radiofrequency voltage $V_{acc}$ is turned off. Simultaneously with this, the application of the radiofrequency voltage $V_{ext}$ to the radiofrequency kicker 70 is started (time T5). It is noted that the start of applying the radiofrequency voltage $V_{ext}$ to the radiofrequency kicker 70 for the radiofrequency kicker 70 (time T5) may not be exactly simultaneous with the moment when the acceleration radiofrequency voltage $V_{acc}$ is turned off. Applying the radiofrequency voltage $V_{ext}$ may be started immediately before, simultaneous with or immediately after the start of interrupting the acceleration radiofrequency wave (time T4), or alternatively immediately before or immediately after the acceleration radiofrequency voltage $V_{acc}$ is turned off.

If the radiofrequency kicker 70 has no resonator structure and is designed such that the electrostatic capacitance has an appropriate value, the radiofrequency voltage of the radiofrequency kicker 70 quickly rises at a response speed of several µs. Here, the betatron oscillations have the property of causing a resonant increase in amplitude, when the product of the circulation frequency of the beam and any one of a tune or a decimal part of a tune is approximately equal to the frequency of the radiofrequency voltage to be applied. Accordingly, the frequency $f_{ext}$ of the radiofrequency voltage in question is set to be approximately equal to the product $\Delta v_r \times f_{rev}$ of a decimal part $\Delta v_r$ of the horizontal tune $v_r$ of the maximum energy beam and a circulation frequency $f_{rev}$ of the maximum energy beam. In consequence, the amplitude of the horizontal betatron oscillations keeps on resonantly increasing and then the beam reaches the peeler magnetic field region 44 and the regenerator magnetic field region 45 (time T6). It is noted that a frequency $f_{ext}$ of a frequency voltage may be set to be equal to the product $\Delta v_r \times f_{rev}$ of the horizontal tune $v_r$ of the maximum energy beam and a circulation frequency $f_{rev}$ of the maximum energy beam.

Upon passage through the peeler magnetic field region 44, the beam is kicker toward the outer circumference, whereas upon passage through the regenerator magnetic field region 45, the beam is kicked toward the inner circumference. Both the peeler magnetic field region 44 and the regenerator magnetic field region 45 have magnetic gradients in the radial direction, so that while the beam is circulating multiple times, the amount of kick gradually increases and the turn separation increases. Thus, the resonance condition of betatron oscillations, $2v_r=2$, can be utilized to increase the turn separation.

The septum coil 43 is installed in the beam extraction path entrance 82. Then, when obtaining the turn separation greatly exceeding the thickness of the coil conductor 43-1 which is installed on the inner circumference side of the septum coil 43, the beam is directed into the inside of the septum coil 4, then sufficiently bent to be directed to the high energy beam transport 47, thereby being extracted.

It is noted that, immediately after the application of radiofrequency voltage to the radiofrequency kicker 70 is started (time T5), the time period to the beam extraction can be reduced by applying the largest possible radiofrequency voltage and quickly increasing the beam amplitude. And, the radiofrequency voltage is dropped immediately before the beam reaches the peeler magnetic field region 44 or the regenerator magnetic field region 45 (time T6), and thus the amount of beam traveling into the peeler magnetic field region 44 and the regenerator magnetic field region 45 is adjusted, thus minutely controlling the beam extraction electric current. In place of dropping the radiofrequency voltage $V_{ext}$, by sweeping the frequency of the radiofrequency wave applied to the radiofrequency kicker 70 or by changing the phase of the radiofrequency wave in question, the beam extraction electric current is able to be modified. This utilizes the property in which the betatron frequency of charged particles contained in the beam varies with a distribution (tune spread). By changing the frequency of the radiofrequency wave, depending on which band in the oscillation frequency distribution of the charged particles causing a resonance is matched, the beam extraction electric current can be modified. Also, in placing of reducing, the radiofrequency voltage $V_{acc}$ may be interrupted.

Then, the beam extraction is stopped (time T7) by stopping the application of the radiofrequency voltage $V_{ext}$ to the radiofrequency kicker 70 after a lapse of time period $t_4$ from the beam extraction start (time T6). Adjusting the time $t_4$ enables control on the beam extraction time.

Controlling the radiofrequency voltage applied to the radiofrequency kicker 70 enables adjustment of beam extraction current, and stopping the application of the radiofrequency voltage in question enables stopping the beam extraction. Therefore, irradiation at a spot dose required in scanning irradiation can be performed with a single extraction of pulse beam without excess and deficiency, and hence a higher dose rate is achieved. For example, if the application of the radiofrequency voltage $V_{ext}$ to the radiofrequency kicker 70 is continued until after a lapse of time period t4' from the beam extraction start (time T6) as illustrated in FIG. 8, the beam can be extracted until time T7'.

Further, if the circulating beam remains in the accelerator after the extraction, the beam extraction can be resumed by reapplying the radiofrequency voltage $V_{ext}$ in question (time T8), and therefore the beam is able to be used for the next spot irradiation without another process of injection, capture and acceleration. Stated another way, multiple beam extractions can be performed within a single acceleration cycle, so that a wasteless use of the charge injected by the ion source 53 is enabled. Because of this, the dose rate is further increased. Then, the acceleration voltage $V_{acc}$ begins rising again, and thereby a new acceleration cycle begins (time T10).

Figure 9:
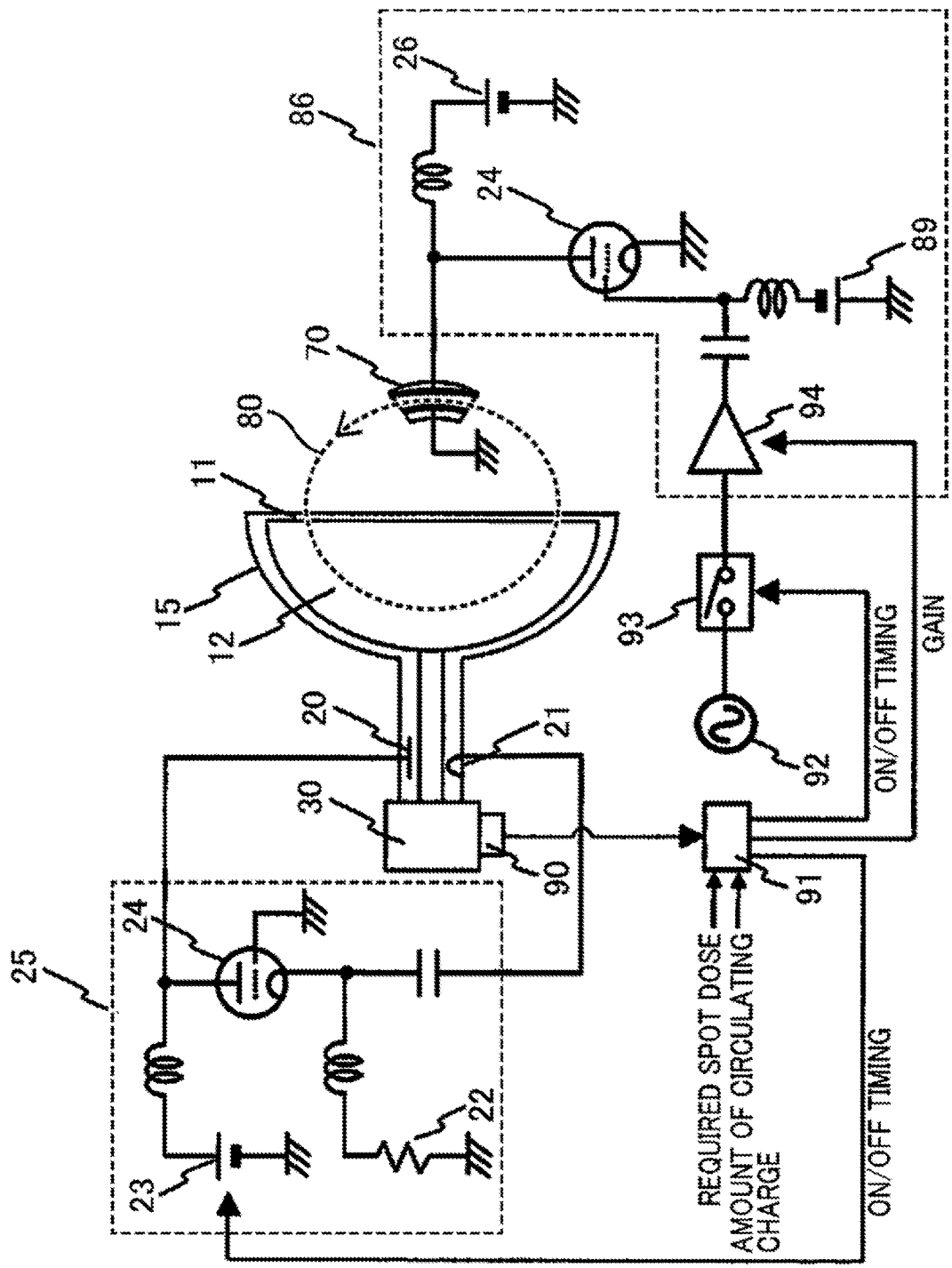
FIG. 9 is a block diagram of an acceleration radiofrequency power supply, a radiofrequency kicker power supply and a control system according to the first embodiment.

FIG. 9 is a block diagram of the radiofrequency power supply and the control system to implement the extraction method described above. The acceleration radiofrequency power supply 25 has cathode resistance 22, a plate power supply 23, and a triode 24. A radiofrequency kicker power supply 86 has a plate power supply 26, a triode 24, a grid bias power supply 89, and a preamplifier 94. FIG. 9 illustrates a configuration in the case of using the radiofrequency kicker power supply 86 together with the triode, but in addition, a tetrode and/or a semiconductor amplifier may be used.

The acceleration radiofrequency power supply 25 may be of a self-oscillation type, which may be operated in a mode in which a portion of the acceleration radiofrequency wave is returned at a pickup loop 21 to a cathode circuit. The radiofrequency acceleration voltage is controlled through fast modulation on the output voltage of the plate power supply 23. The cathode bias potential is given in the form of dividing the plate potential by the cathode resistance 22 as illustrated in FIG. 9, or alternatively given by use of the cathode power supply.

An original oscillator 92 generates a signal in a certain frequency band for the radiofrequency kicker 70. Here, assuming that the signal of the original oscillator 92 includes a required frequency band component with consideration given to the beam tune spread and variations of the horizontal tune during the application of radiofrequency voltage to the radiofrequency kicker 70. The signal in question passes through a switch 93, then is amplified at the preamplifier 94, then is amplified at the triode 24, and then is provided to the radiofrequency kicker 70. The radiofrequency voltage of the radiofrequency kicker 70 is controlled by changing the gain of the preamplifier 94, or alternatively through fast modulation on the output voltage of the plate power supply 26.

A computing unit 91 controls ON/OFF timing and voltage amplitude of an acceleration radiofrequency wave and ON/OFF timing and voltage amplitude of the radiofrequency kicker 70, based on a frequency modulation pattern of an acceleration radiofrequency wave detected either by an angle detection mechanism 90 of the rotating capacitor 30 or from an acceleration radiofrequency pickup signal, and based on a required dose to each irradiation spot.

Also, a beam monitor for electrostatically or magnetically detecting the amount of beam charge is installed somewhere on the maximum energy orbit 80 in order to monitor the amount of circulating charge remaining inside the accelerator. And, when the amount of circulating charge is reduced to or below a certain level, the computing unit 91 starts application of acceleration voltage again to repeat the acceleration cycle of capture, acceleration and extraction.

Figure 10:
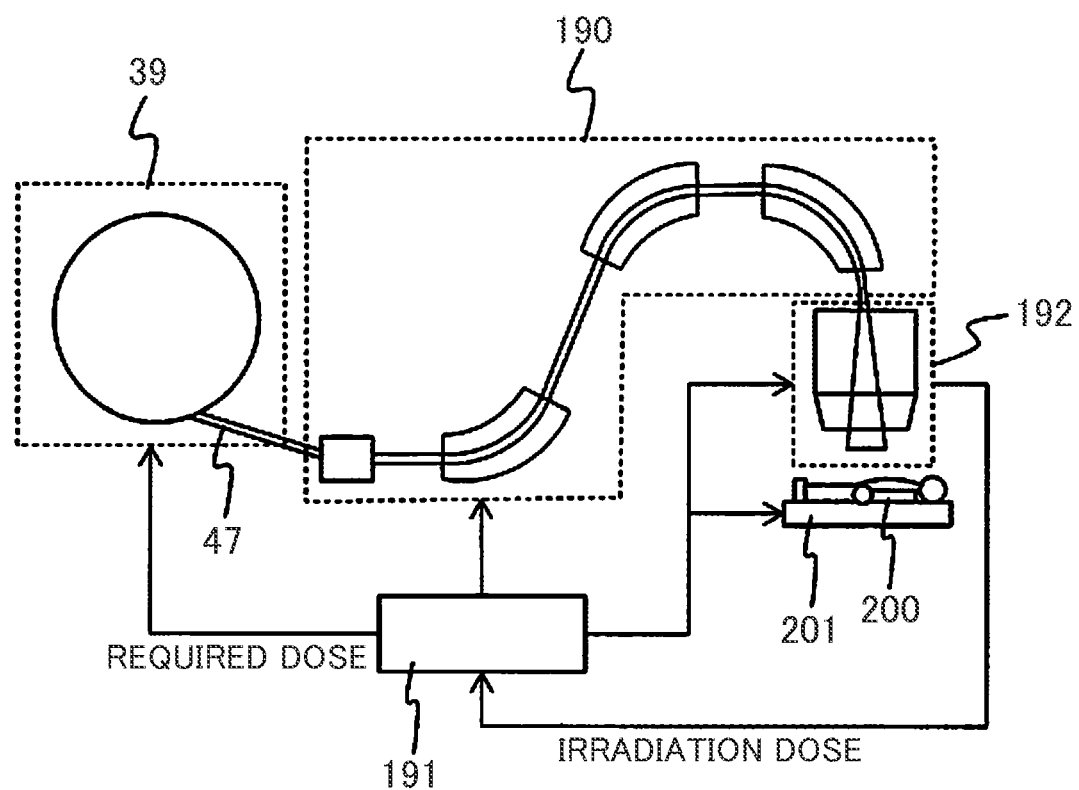
FIG. 10 is a diagram illustrating the overall configuration of a particle therapy system according to the first embodiment.

FIG. 10 illustrates the overall configuration of a particle therapy system. In FIG. 10, the particle therapy system includes the circular accelerator 39, a rotating gantry 190, an irradiation system 192 including a scanning coil, a treatment table 201 and a controller 191 controlling them. The beam extracted from the circular accelerator 39 is transported to the irradiation system 192 by the rotating gantry 190. The transported ion beam is shaped conformally to a target shape by the irradiation system 192 and by adjusting the beam energy, and then a predetermined dose of beam irradiation is applied to a target area of a patient 200 lying on the treatment table 201. The irradiation system 192 incorporates a dose monitor to monitor a dose applied to the patient 200 on each irradiation spot. Based on the dose data, the controller 191 calculates a require dose to each irradiation spot, to obtain input data to the computing unit 91 in FIG. 9.

The first embodiment has been described. According to the embodiment, stopping the radiofrequency application at the radiofrequency kicker 70 in midstream prevents the beam from reaching the peeler magnetic field region 44 and the regenerator magnetic field region 45, enabling interruption of beam extraction from the circular accelerator 39. By resuming the application to the radiofrequency kicker 70, the beam extraction is also able to be resumed without another process of reinjection, recapture and reacceleration. Further, the intensity of beam to be extracted from the circular accelerator 39 is able to be controlled by controlling any one of intensity of voltage to be applied to the radiofrequency kicker 70, an amplitude, a phase and a frequency of the radiofrequency wave. Further, by adjusting the voltage to be applied to the radiofrequency kicker 70, factors exerting influences on the beam stabilities are absorbed to achieve stable beam extraction. State another way, the radiofrequency wave used in extraction is used to control the extracted beam charge in each acceleration cycle with high precision. Because of this, dose control suitable for scanning is enabled. In consequence, an increase in dose rate, a reduction in irradiation time period, and an enhancement in patient throughput in the particle therapy system are enabled.

Second Embodiment

A circular accelerator according to a second embodiment will be described. In the embodiment, a description of the same configurations as those in the first embodiment is omitted and only different configurations are described.

In the embodiment, for the purpose of arbitrarily changing the beam energy in a range from 70 MeV to 235 MeV for extraction from an accelerator, an eccentric orbit accelerator is used to form a main magnetic field such that a beam orbit is eccentric toward the beam extraction path entrance 82.

Figure 11:
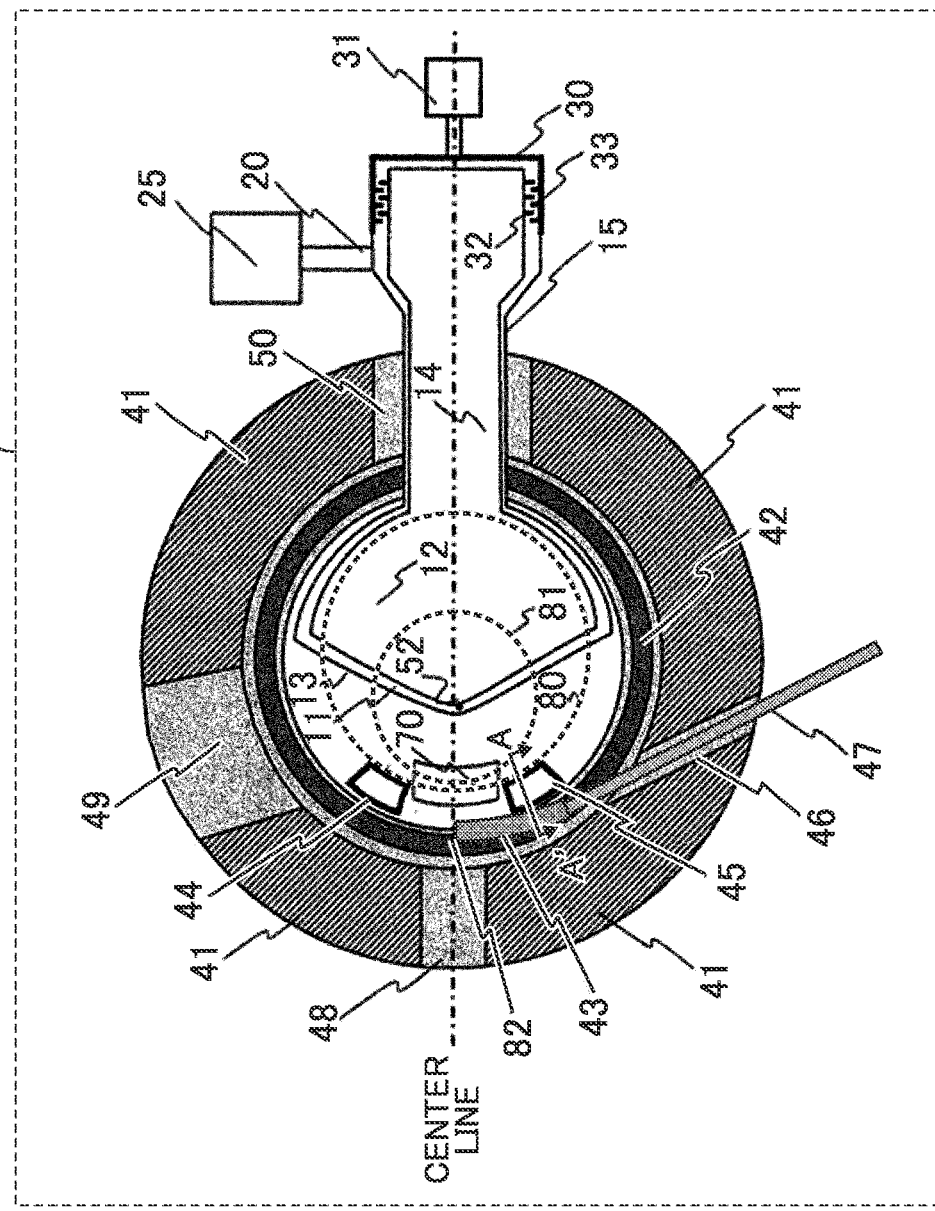
FIG. 11 is a cross-sectional structure of a circular accelerator according to a second embodiment.
Figure 13:
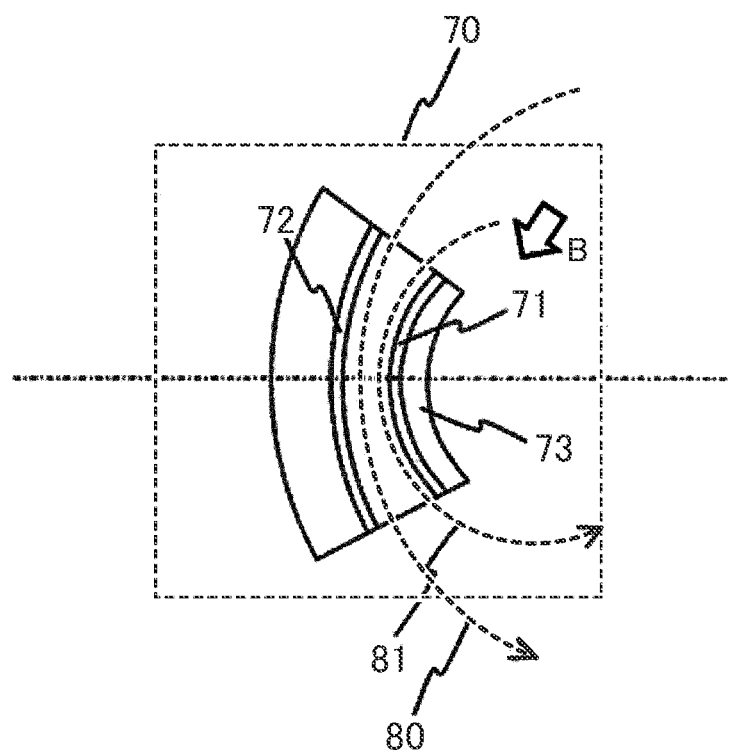
FIG. 13 is a cross sectional structure of a radiofrequency kicker according to the second embodiment.

FIG. 11 illustrates a cross-sectional structure of an eccentric orbit accelerator. Configuration changes from FIG. 2 include the shapes of the dee electrode 12 and the dummy dee electrode 13 and the shape of the acceleration gap 11 created between them. Here, assuming that the line passing through the rotation axis of the rotating capacitor 30 and the center of the circle of the acceleration region is a center line. The ion injector 52 is mounted, on the center line, in a position toward the beam extraction path entrance 82 with respect to the center of the acceleration region. Although not shown, the vertically opposite faces of the main magnetic poles 38 are also significantly different in shapes from that in the first embodiment in order to form a magnetic field described later. The configuration of the radiofrequency kicker 70 differs as illustrated in FIG. 13.

Figure 12:
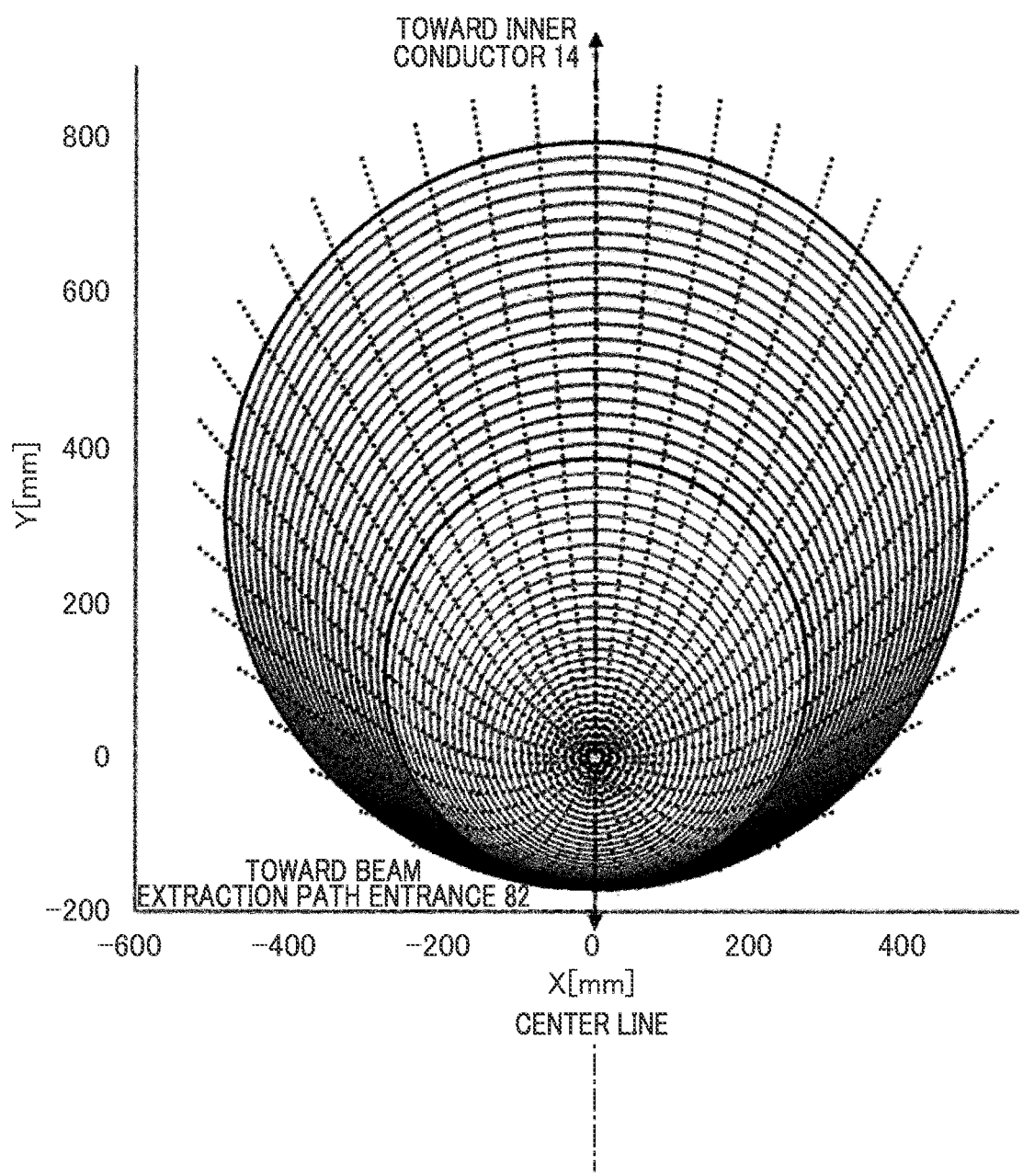
FIG. 12 is a chart illustrating beam orbits from energy to energy in the circular accelerator according to the second embodiment.

FIG. 12 illustrates orbits for each energy and describes the method of implementing eccentric orbits. For closed orbits, orbits in 50 energy levels are shown at intervals of magnetic rigidity 0.04 Tm from the maximum energy 235 MeV by solid lines. Each dot line shows a line connecting the same orbital phases on each orbit, which is referred to as an equal orbital phase line. The equal orbital phase lines are plotted every orbital phase $\pi/20$ from an intensive region. The acceleration gap 11 formed between the dee electrode 12 and the opposite dummy dee electrode 13 is installed along the equal orbital phase line. More specifically, the dee electrode 12 has a fan-like, hollow shape with a distal end located proximal to the center of concentric orbits, and a radius along the equal orbital phase line. Also, the dummy dee electrode 13 has a shape facing the dee electrode 12.

In a low energy beam region, the orbits are analogous to concentric orbits centered at near the ion injector 52 similarly to cyclotrons. And, the higher energy orbits densely gather around the beam extraction path entrance 82, but, around the inner conductor 14, the orbits of respective energies have a positional relationship of separating from each other. The point where the orbits densely gather is referred to as an intensive region, and the region where the orbits separate is referred to as a separate region. In such orbit arrangement, the beam is extracted from around the intensive region, so that a required amount of beam kick can be decreased, thereby facilitating energy variable beam extraction.

Because of the orbit configuration and stable oscillations occurring around the orbit as described above, in the accelerator according to the embodiment, a distribution in which the main magnetic field diminishes gradually toward the outer circumference in the radial direction is formed by use of the shape of the main magnetic poles 38 and the trim coils and/or the pole pieces installed thereon. Further, on a line along the design orbit, the main magnetic field takes a constant value. Accordingly, the design orbit is a circle.

A method of extracting beam is described below. The beam extraction is performed by use of: the radiofrequency kicker 70 located around the intensive region where beam orbits of all extraction energies gather; the peeler magnetic field region 44 and the regenerator magnetic field region 45 located on opposite sides thereof; the septum coil 43; and the high energy beam transport 47. In the embodiment, the radiofrequency kicker 70 of the above-described elements used for extraction differs in configuration from that in the first embodiment.

FIG. 13 is a cross sectional structure of the radiofrequency kicker 70 according to the embodiment. The radiofrequency kicker 70 includes the ground electrodes 71, the protrusions 73 and the high voltage electrodes 72 as in the case of the first embodiment, but the ground electrodes 71 and the high voltage electrodes 72 are placed to sandwich the maximum energy orbit 80 and a minimum extraction energy orbit 81. And also, shapes of the ground electrodes 71 and the high voltage electrodes 72 are defined to allow the radiofrequency electric field to act in a direction close to a direction perpendicular to each orbit in orbit plane. Specifically, the ground electrodes 71 and the high voltage electrodes 72 are shaped to be arranged approximately parallel to each other along curves of the minimum extraction energy orbit 81 and the maximum energy orbit 80. Here, the minimum extraction energy orbit 81 is an orbit through which beam of a minimum energy (e.g., 70 MeV) extractable from the circular accelerator 39 passes. It is noted that the protrusions 73 may be omitted.

The beam extraction procedure is the same on principle as that described in the first embodiment, but if the timing for interrupting the acceleration radiofrequency voltage $V_{acc}$ (time T4), and the timing for starting application of the radiofrequency voltage $V_{ext}$ to the radiofrequency kicker 70 (time T5) are shifted earlier in time, any energy beam can be extracted. In other words, at the time when the accelerated beam reaches a desired energy, the interruption of the acceleration radiofrequency voltage $V_{acc}$ is started (time T4). Thereby, the beam acceleration is interrupted. Then, by starting the application of the radiofrequency voltage $V_{ext}$ (time T5), the amplitude of the betatron oscillations of the desired energy beam is increased by the radiofrequency kicker 70. Then, this beam reaches the peeler magnetic field region 44 and the regenerator magnetic field region 45, which is then extracted.

Also, for the septum coil 43 and the coil located in the high energy beam transport 47 to adjust optical parameters, an excitation current is required to be varied according to beam energy to be extracted. Therefore, for these coils, an air core structure or a laminated steel core may be used to configure a coil of approximately from a single turn to several turns to be energized by pulses. The septum coil 43 may be placed by being divided into two or more divisions in the beam travel direction.

The second embodiment has been described. According to the description of the second embodiment, advantageous effects as in the case of those in the first embodiment can be offered. Further, by achieving such a configuration as described above, the circular accelerator 39 according to the present invention is capable of extracting beam of variable energy without need for a degrader. Because of this, a current value of beam lost at the time of extraction can be minimized to increase the beam use efficiency, thereby realizing a higher dose rate than the first embodiment. Also, an electrical change to the extraction energy is enabled, so that the advantage of a shorter time required for energy switching than the mode of mechanically moving a degrader is possessed.

LIST OF REFERENCE SIGNS

10 . . . Radiofrequency acceleration cavity
11 . . . Acceleration gap
12 . . . Dee electrode
13 . . . Dummy dee electrode
14 . . . Inner conductor
15 . . . Outer conductor
20 . . . Input coupler
21 . . . Pickup loop
22 . . . Cathode resistance
23 . . . Plate power supply
24 . . . Triode
25 . . . Acceleration radiofrequency power supply
26 . . . Plate power supply
30 . . . Rotating capacitor
31 . . . Motor
32 . . . Stationary electrode
33 . . . Rotating electrode
36 . . . Magnetic field gradient shim
37 . . . Magnetic field correction shim
38 . . . Main magnetic pole
39 . . . Circular accelerator
40 . . . Main electromagnet
41 . . . Yoke
42 . . . Main coil
43 . . . Septum coil
44 . . . Peeler magnetic field region
45 . . . Regenerator magnetic field region
46 . . . Beam through port
47 . . . High energy beam transport
48 . . . Coil through port
49 . . . Vacuuming through port
50 . . . Radiofrequency through port
52 . . . Ion injector
53 . . . Ion source
54 . . . Low energy beam transport
60 . . . Cryostat
70 . . . Radiofrequency kicker
71 . . . Ground electrode
72 . . . High voltage electrode
73 . . . Protrusion
80 . . . Maximum energy orbit
81 . . . Minimum extraction energy orbit
82 . . . Beam Extraction path entrance
86 . . . Radiofrequency kicker power supply
89 . . . Grid bias power supply
90 . . . Angle detection mechanism
91 . . . Computing unit
92 . . . Original oscillator
93 . . . Switch
94 . . . Preamplifier
190 . . . Rotating gantry
191 . . . Controller
192 . . . Irradiation system
200 . . . Patient
201 . . . Treatment table

The invention claimed is:

1. A circular accelerator that applies a first radiofrequency wave in a main magnetic field in order to accelerate charged particle beam while increasing an orbit radius comprising,
a radiofrequency acceleration cavity configured to generate the first radiofrequency wave;
a radiofrequency kicker configured to generate a second radiofrequency wave;
wherein the second radiofrequency wave has a frequency different from the first radiofrequency wave and is applied in an intensive region of the orbit of the charged particle beam inside the circular accelerator, or on the maximum energy orbit of the charged particle beam in order to extract the charged particle beam,
wherein the second radiofrequency wave is applied in a direction perpendicular to the orbit in an orbit plane.

2. The circular accelerator according to claim 1, comprising:
the radiofrequency kicker which includes a high voltage electrode and a ground electrode for application of the second radiofrequency wave,
wherein the high voltage electrode and the ground electrode are located on opposite sides of an orbit through which the charged particle beam accelerated to a desired energy travels.

3. The circular accelerator according to claim 2, wherein the second radiofrequency wave is a frequency at which amplitude of betatron oscillations in an orbit plane of the charged particle beam and also in a horizontal direction which is a direction perpendicular to orbit of the charged particle beam.

4. The circular accelerator according to claim 3, wherein the second radiofrequency wave includes a frequency component that is approximately equal to a product of a circulation frequency of the charged particle beam of the desired energy and any one of an oscillation frequency of the betatron oscillations in the horizontal direction or a decimal part of the oscillation frequency.

5. The circular accelerator according to claim 1, wherein a magnetic field region in which a multipole magnetic field including a magnetic field component with two or more poles and at least quadrupole magnetic field component is in existence, is in at least two places in the main magnetic field.

6. The circular accelerator according to claim 5, wherein a multipole magnetic field component with four or more poles, included in the magnetic field region, is a first magnetic field region having a magnetic field gradient at which the main magnetic field strengthens toward an outer circumference in a radial direction.

7. The circular accelerator according to claim 6, wherein a multipole magnetic field component with four or more poles, included in the magnetic field region, is a second magnetic field region having a magnetic field gradient at which the main magnetic field weakens toward an outer circumference in a radial direction.

8. The circular accelerator according to claim 7, wherein the first magnetic field region and the second magnetic field region exist on the outer circumference side of an orbit along which the charged particle beam under acceleration circulates.

9. The circular accelerator according to claim 7, wherein when the charged particle beam is accelerated to a desired energy, the first radiofrequency wave is interrupted and the second radiofrequency wave rises.

10. The circular accelerator according to claim 9, wherein before beam reaches either the first magnetic field region or the second magnetic field region after starting application of the radiofrequency wave used for the extraction, a voltage of the second radiofrequency is controlled to be either decreased or interrupted.

11. The circular accelerator according to claim 10, wherein a time period during application of the second radiofrequency wave is changed or the second radiofrequency wave is reapplied after interruption.

12. The circular accelerator according to claim 1, comprising:
- a main electromagnet that forms the main magnetic field and includes main magnetic poles placed to face each other;
- an ion source that injects the charged particle beam into between the main magnetic poles;
- an acceleration gap that is located between the main magnetic poles, the first radiofrequency wave being applied to the acceleration gap; and
- an extraction path through which the charged particle beam is extracted from the main magnetic field to outside of the circular accelerator,
- wherein the acceleration gap allows frequency modulation to be performed on the first radiofrequency wave.

13. The circular accelerator according to claim 1, comprising:
- a main electromagnet that forms the main magnetic field and includes main magnetic poles placed to face each other;
- an ion source that injects the charged particle beam into between the main magnetic poles;
- an acceleration gap that is located between the main magnetic poles, the first radiofrequency wave being applied to the acceleration gap; and
- an extraction path through which the charged particle beam is extracted from the main magnetic field to outside of the circular accelerator,
- wherein orbit on which the charged particle beam circulates is eccentric in a certain direction.

14. A particle therapy system, comprising:
the circular accelerator according to claim 1; and
an irradiation system that irradiates a patient with a beam.

15. The circular accelerator according to claim 1, wherein the main magnetic field comprises an Azimuthal Varying Field.

16. The circular accelerator according to claim 1, wherein the main magnetic field is a main magnetic field of temporally constant intensity.

* * * * *